United States Patent
Saleem

(10) Patent No.: US 10,386,336 B2
(45) Date of Patent: Aug. 20, 2019

(54) ULTRASONIC PULSE VELOCITY TESTER

(71) Applicant: University of Dammam, Dammam (SA)

(72) Inventor: Muhammad Saleem, Dammam (SA)

(73) Assignee: Imam Abdulrahman bin Faisal University, Dammam (SA)

( * ) Notice: Subject to any disclaimer, the term of this patent is extended or adjusted under 35 U.S.C. 154(b) by 198 days.

(21) Appl. No.: 15/245,997

(22) Filed: Aug. 24, 2016

(65) Prior Publication Data

US 2018/0059062 A1    Mar. 1, 2018

(51) Int. Cl.
| | | |
|---|---|---|
| *G01N 3/34* | (2006.01) | |
| *G01N 29/04* | (2006.01) | |
| *G01N 29/07* | (2006.01) | |
| *G01N 29/44* | (2006.01) | |
| *G01N 33/38* | (2006.01) | |

(52) U.S. Cl.
CPC .............. *G01N 29/07* (2013.01); *G01N 3/34* (2013.01); *G01N 29/045* (2013.01);
(Continued)

(58) Field of Classification Search
CPC ........ G01N 29/07; G01N 3/34; G01N 33/383; G01N 2291/0232; G01N 29/449; G01N 29/4427; G01N 29/045
See application file for complete search history.

(56) References Cited

U.S. PATENT DOCUMENTS

| | | | | |
|---|---|---|---|---|
| 6,250,159 B1 * | 6/2001 | Kreier | ................... | G01N 29/07 |
| | | | | 73/602 |
| 2011/0167754 A1 | 7/2011 | Dubon et al. | | |

(Continued)

FOREIGN PATENT DOCUMENTS

| | | | |
|---|---|---|---|
| JP | 2002071507 A | * | 3/2002 |
| WO | WO 2011/132024 A1 | | 10/2011 |
| WO | WO 2015/168170 A1 | | 11/2015 |

OTHER PUBLICATIONS

K. Streeter, et al., "Mechanical anchor strength in stone masonry" https://ncptt.nps.gov/wp-content/uploads/2008-05.pdf, 2008, pp. 1-38.

(Continued)

*Primary Examiner* — Justin Seo
*Assistant Examiner* — John M Royston
(74) *Attorney, Agent, or Firm* — Oblon, McClelland, Maier & Neustadt, L.L.P.

(57) ABSTRACT

An apparatus for detecting anchor bolt pullout strength. The apparatus includes circuitry configured to process ultrasonic measurement signals using at least one of a direct, an indirect, and a semi-direct measurement technique. Further, the apparatus comprises a first probe and a second probe connected to the circuitry, and memory for storing data detected by the first and the second probe. The memory is connected to the circuitry and a data connection connected to the circuitry and configured to communicate with an external network. An ultrasonic signal is transmitted by the circuitry through the first probe and rebounded by the second prob. The circuitry detects a time duration to receive the rebounded signal, storing the time duration to the memory, and comparing the time duration to reference measurement data. The reference measurement data may be stored in at least one of the memory and the external network.

7 Claims, 12 Drawing Sheets

(52) U.S. Cl.
CPC ....... *G01N 29/449* (2013.01); *G01N 29/4427* (2013.01); *G01N 33/383* (2013.01); *G01N 2291/0232* (2013.01)

(56) References Cited

U.S. PATENT DOCUMENTS

| | | | | |
|---|---|---|---|---|
| 2014/0020468 A1* | 1/2014 | Smith | ................... | B06B 1/0207 |
| | | | | 73/597 |
| 2015/0160167 A1* | 6/2015 | Kawasaki | ............ | G01N 29/069 |
| | | | | 73/598 |
| 2015/0309007 A1* | 10/2015 | Bellotti | ................ | G01N 29/348 |
| | | | | 73/597 |
| 2016/0202216 A1* | 7/2016 | Komiya | ................. | G01N 29/07 |
| | | | | 73/598 |
| 2017/0268915 A1* | 9/2017 | Gestner | ................... | G01F 1/662 |

OTHER PUBLICATIONS

B&S Directorate Research Designs and Standards Organisation, Lucknow, "Guidelines on non-destructive testing of bridges", http://www.rdso.indianrailways.gov.in/uploads/files/1296882621315-bs_103.pdf, Aug. 2009, pp. 1-133.

J.S.Popovics, "Non-destructive assessment of concrete structures: reliability and limits of Single and combined techniques" http://www.rilem.org/docs/2013112104_207-inr-unedited-version.pdf, 2012, pp. 1-485.

\* cited by examiner

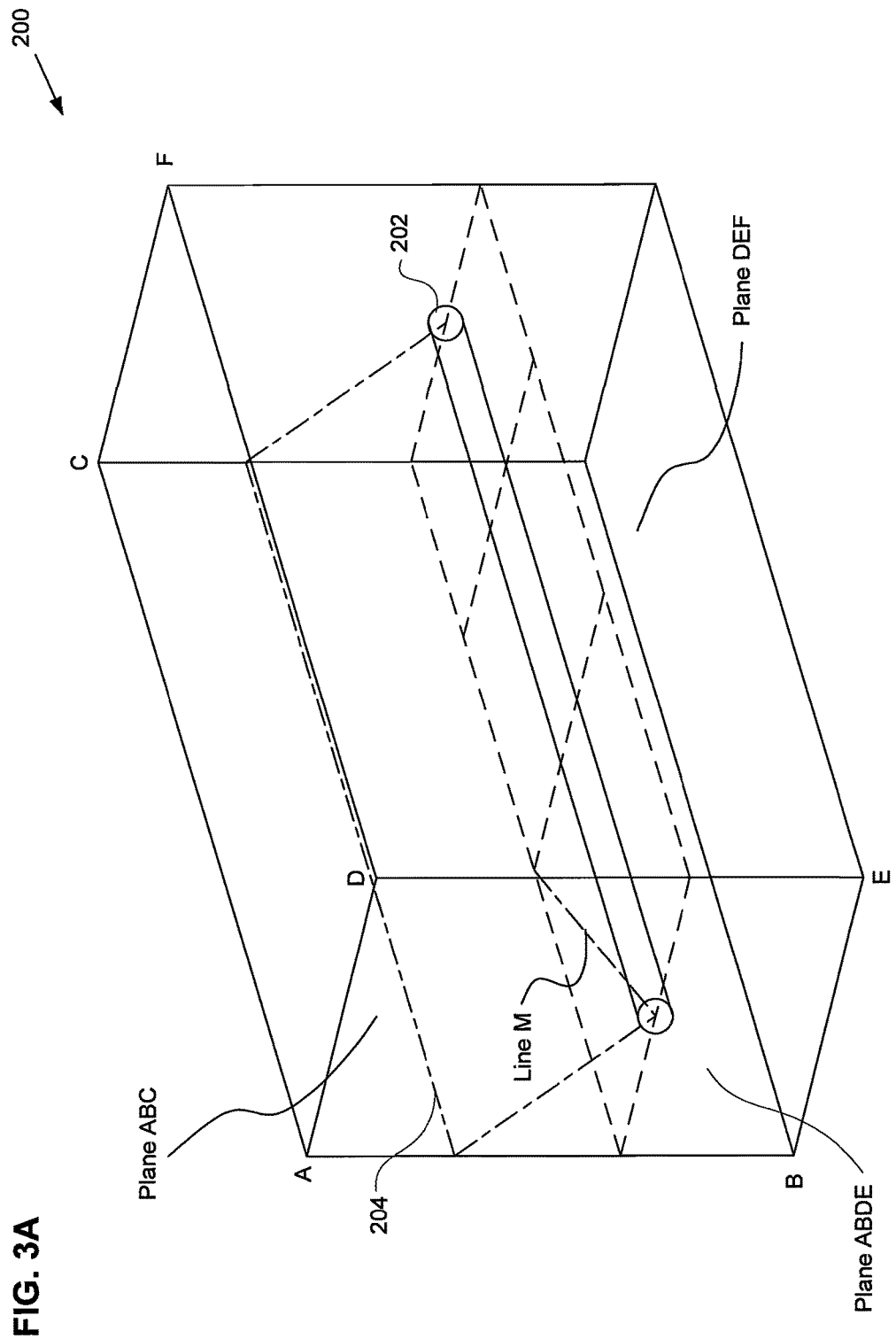

ULTRASONIC PULSE VELOCITY TESTER

BACKGROUND

Field of the Disclosure

The present disclosure is directed toward an ultrasonic pulse velocity testing system and method.

Description of the Related Art

Degradation and failure of reinforced concrete structures can occur in a variety of ways including, for example through formation of voids and cracks during manufacture, construction, and use. The result may be weakened reinforced concrete structures that are functionally and quantifiably inferior but not visibly differentiated from reinforced concrete structures of full strength. For these reasons it is important that improved methods and apparatus for inspection and detection of concrete be further developed with the aim of reducing the frequency and severity of potential structural failures of reinforced structural concrete construction.

SUMMARY

The present disclosure is directed to an apparatus for detecting anchor bolt pullout strength. The apparatus includes circuitry configured to process ultrasonic measurement signals using at least one of a direct, an indirect, and a semi-direct measurement technique. Further, the apparatus comprises a first probe and a second probe connected to the circuitry, and memory for storing data detected by the first and the second probe. The memory is connected to the circuitry and a data connection connected to the circuitry and configured to communicate with an external network.

An ultrasonic signal is transmitted by the circuitry through the first probe and rebounded by the second prob. The circuitry detects a time duration to receive the rebounded signal, storing the time duration to the memory, and comparing the time duration to reference measurement data. The reference measurement data may be stored in at least one of the memory and the external network.

The foregoing general description of the illustrative implementations and the following detailed description thereof are merely exemplary aspects of the teachings of this disclosure, and are not restrictive.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings wherein:

FIG. 3A is a diagram indicating placement positions for a first probe and a second probe about a reinforced concrete reference specimen for measurement of USPV signals, according to one example;

DETAILED DESCRIPTION OF THE EMBODIMENTS

Figure 1:
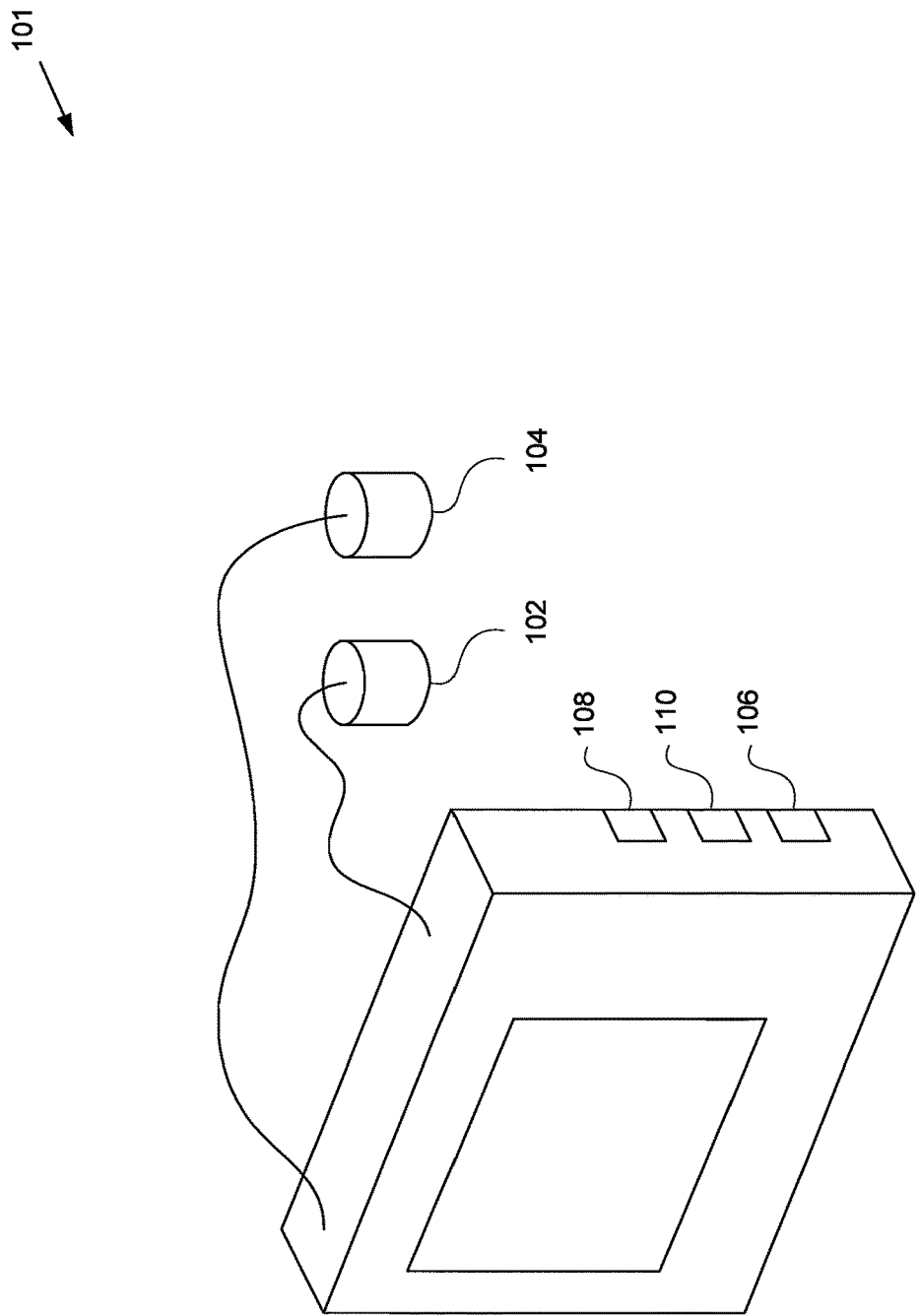
FIG. 1 is perspective view of a Ultrasonic Pulse Velocity (USPV) test device, according to one example.

In the drawings, like reference numerals designate identical or corresponding parts throughout the several views. Further, as used herein, the words "a", "an" and the like generally carry a meaning of "one or more", unless stated otherwise.

Referring now to the drawings, wherein like reference numerals designate identical or corresponding parts throughout the several views.

FIG. 1 is perspective view of a USPV test device 101, according to one example. The USPV test device 101 includes a first probe 102, a second probe 104, a circuitry 106, and a communication link 110. Further, the USPV test device 101 may also include a Schmidt Hammer 118 (not shown) and be configured to perform Schmidt Hammer tests to estimate compressive strength of a reinforced concrete reference specimen 200. The USPV test device 101 may also have at least one of a memory 108 for storage of data readings and a maximum likelihood detector 120.

Further, the USPV test device 101 may be configured to have reference measurement data embedded within the circuitry 106, provided by the memory 108, or connected to an external network 140, for example a database, a network location, or a data storage device, to obtain reference measurement data as needed. The reference measurement data may then be compared with ultrasonic measurements detected by the first probe 102 and the second probe 104 of the USPV test device 101.

The maximum likelihood detector 120 may be embedded within the circuitry 106 or it may be remotely accessed by the circuitry 106.

Figure 2:
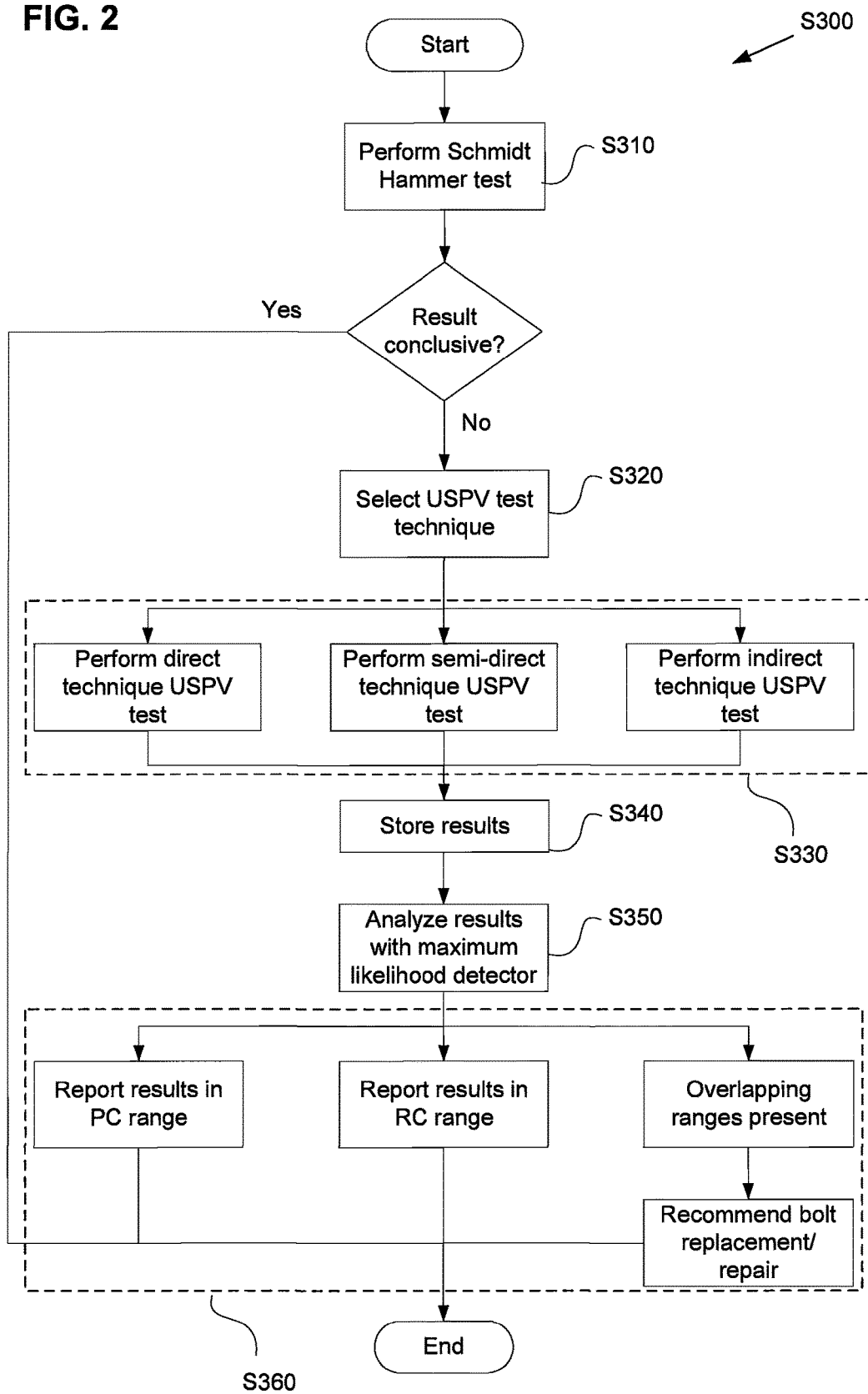
FIG. 2 is a process diagram for operation of the USPV test device, according to one example.

FIG. 2 is a process diagram for operation of the USPV test device 101, according to one example. The process diagram includes a sequence of primary processes S300 of a method for estimation of the quality of a bond between concrete and embedded reinforcement, therefore serving as a proxy for estimated compressive strength of reinforced concrete and for pullout strength of an anchor bolt 130 embedded in concrete. The diagram encompasses various operations of the system examples and embodiments described by FIG. 1 through FIG. 5. The method for estimation of load capacity of reinforced concrete S300 includes, in this example, an optional Schmidt Hammer-type test process S310, a process of selecting a USPV test technique S320, a process for performing one of a direct technique USPV test, a semi-direct technique USPV test, or an indirect technique USPV test 330, a process of storing test data S340, an optional process of analyzing results with a maximum likelihood detector S350, and a process for reporting results and recommendations S360.

S310 represents a process of testing reinforced concrete with USPV test device 101 configured to measure compressive strength of concrete using, for example, a Schmidt Hammer technique. In one example, a Schmidt Hammer test result deemed by the USPV test device 101 to be conclusive may not require that a USPV test be conducted. The Schmidt Hammer test may be deemed conclusive if, for example, a mean of rebound number readings exceeds a desired value. However, if the USPV test device 101 deems the Schmidt Hammer test result is not sufficiently conclusive, for example the mean of rebound number readings is less than the desired value or is within a range of values considered uncertain, the USPV test may be conducted to confirm the result of the Schmidt Hammer test.

S320 represents a process of selecting a USPV test technique. The USPV test technique selected may depend on available access to the structure or specimen to be tested. In one case, if two opposite sides of the structure are accessible for placement of the first probe 102 on a first side and the second probe 104 on a second side, the direct USPV technique may be selected. In another case, if only one side of the structure is accessible for placement of the first probe 102, the indirect USPV technique may be selected. In another case if a first side of the structure is accessible for placement of the first probe 102 and a third side perpendicular to the first side and surrounding the end of a specimen reinforcement 202 is available for placement of the second probe 104, the semi-direct USPV technique may be selected. The USPV test device 101 may be configured to provide an indication of whether repair or replacement is recommended based on, for example, historical data of past inspections of the particular reinforced concrete reference specimen 200 or of similar measurement results.

S330 represents a process of performing at least one of a plurality of USPV measurements using the USPV test device 101 configured to perform at least one of a direct ultrasonic measurement technique, a semi-direct ultrasonic measurement technique, and an indirect ultrasonic measurement technique.

S330 represents a process of storing USPV measurements as data. The USPV test device 101 may be configured to send and receive ultrasonic measurement data based on a position of at least one of the first probe 102 and the second probe 104. Further, the USPV test device 101 may record the ultrasonic measurement data to the memory 108 or transmit the ultrasonic measurement data detected to an external location external network 140.

S350 represents an optional process of analyzing ultrasonic measurement readings of the USPV test device 101. The process of analyzing ultrasonic measurement data may be built into the circuitry 106 of the USPV test device 101 or may reside in the external network 140 that the circuitry 106 may be in communication with. The resulting analysis may produce a discrete digital output value for each ultrasonic data reading and/or a mean ultrasonic data reading based on a probability or likelihood of the signal of each ultrasonic data reading detected by the circuitry 106.

S360 represents a process of reporting test results with a USPV test device 101 configured to provide an indication of at least one of ultrasonic measurements, a graphical plot of time and velocity measurements indicating pure concrete (PC) zone and reinforced concrete (RC) zone measurements, including any applicable overlap between the two regions, and recommended actions.

Indications may be obtained by comparing reference data within the memory 108 or obtained from another location, such as from the external network 140, and measurements obtained by the USPV test device 101 through USPV measurements, using the first probe 102 and the second probe 104. Reference data may be obtained as described by FIG. 6.

In a case where the ultrasonic measurements for the PC zone and the RC zone indicate there is overlap, the USPV test device 101 may indicate to an user there is overlap and that the quality of the bond for that particular anchor bolt 130 is not sufficient. Depending on the magnitude of overlap, the USPV test device 101 may recommend to the user that the anchor bolt 130 be examined, repaired, or replaced. Indication of the recommendation may be in at least one of several forms, for example audio, visual, and haptic indications from the USPV test device 101, and transmission of one or more messages to the external network 140.

FIG. 3A is a diagram indicating placement positions for the first probe 102 and the second probe 104 about a reinforced concrete reference specimen 200 for measurement of USPV signals, according to one example. The reinforced concrete reference specimen 200 includes a specimen reinforcement 202.

In one example, a direct technique of measurement of USPV signals, the first probe 102 and the second probe 104 are disposed on a first plane (ABC) and a second plane (DEF) of the reinforced concrete reference specimen 200, respectively, along axes substantially parallel to that of the specimen reinforcement 202. Two sets of ultrasonic measurements are taken, one for a PC zone and one for a RC zone. Ultrasonic measurements in the PC zone may be made along an axis 204 substantially parallel to the specimen reinforcement 202 and disposed a vertical distance from the specimen reinforcement 202 such that the specimen reinforcement 202 does not affect USPV signals transmitted along substantially horizontal axes, for example along various axes between the first probe 102 and the second probe 104 that are substantially parallel to a line AD. Ultrasonic measurements in the RC zone may be made along axes disposed in the first plane (ABC) and the second plane (DEF), respectively, that are substantially parallel to the specimen reinforcement 202 such that the specimen reinforcement 202 does affect the USPV signals transmitted along substantially horizontal axes, for example axes substantially parallel to a line AD, located between the first probe 102 and the second probe 104 and intersecting the longitudinal axis of the specimen reinforcement 202.

An ultrasonic signal may be transmitted from the first probe 102 and rebounded by the second probe 104. The time it takes the signal to be detected serves as an indicator of signal impedance. This is because ultrasound signals cannot pass through porous or air gaps as quickly as through solid material, so more time is needed to detect a signal rebound.

In another example, an indirect technique of ultrasonic measurement of USPV signals, both the first probe 102 and the second probe 104 are disposed on the first plane (ABC) of the reinforced concrete reference specimen 200, along an axis substantially parallel to that of the specimen reinforcement 202. Two sets of ultrasonic measurements are taken, one for the PC zone and one for the RC zone. PC zone ultrasonic measurements may be made along an axis, for example the line 204, parallel to the specimen reinforcement 202 and disposed a vertical distance from the specimen reinforcement 202 such that the specimen reinforcement 202 does not affect the USPV signals transmitted and received by the first probe 102 and the second probe 104, for example along axes in a plane parallel to the plane ADC. RC zone ultrasonic measurements may be made along axes that are parallel to the specimen reinforcement 202 such that the specimen reinforcement 202 does affect the USPV signals transmitted and received by the first probe 102 and the second probe 104, for example in a plane parallel to the plane ADC that intersects the specimen reinforcement 202. An ultrasonic signal may be transmitted from the first probe 102 and rebounded by the second probe 104.

In another example, a semi-direct technique of ultrasonic measurement of USPV signals, the first probe 102 may be disposed on the first plane (ABC) of the reinforced concrete reference specimen 200 substantially parallel to that of the specimen reinforcement 202, and the second probe 104 may be disposed on a third plane (ABD) of the reinforced concrete reference specimen 200 substantially perpendicular to the specimen reinforcement 202. The second probe 104 is in contact with an end of the specimen reinforcement 202 while RC ultrasonic measurements made with the first probe 102 may be performed on the first plane ABC or the second plane DEF along an axis substantially parallel to the specimen reinforcement 202 and disposed a substantially similar vertical distance above the line BE as the vertical distance the specimen reinforcement 202 is disposed above the line BE. An ultrasonic signal may be transmitted from the first probe 102 along the axis and rebounded by the second probe 104.

Figure 3B:
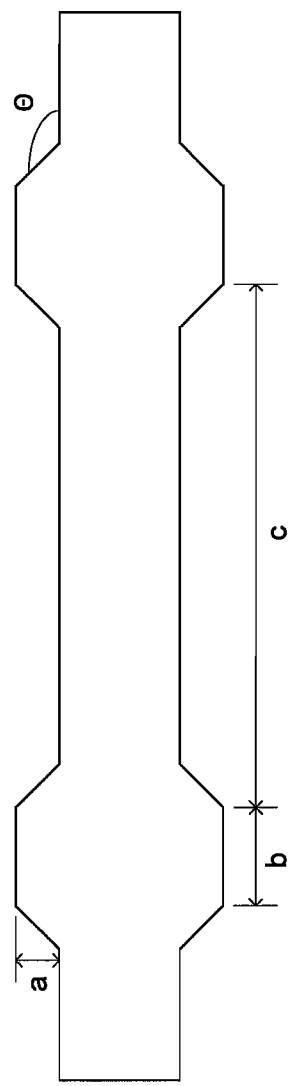
FIG. 3B is a diagram illustrating an example specimen reinforcement 202a that may be cast within a reinforced concrete reference specimen 200a, according to one example.

FIG. 3B is a diagram illustrating an example specimen reinforcement 202a that may be cast within a reinforced concrete reference specimen 200a, according to one example. In one example, the specimen reinforcement 202a may have a rib height a of less than 0.05d and 0.1c, a rib angle θ of less than 45°, a rib width b and rib spacing c, the specimen reinforcement 202a having a relatively small rib height a and large rib spacing c with a low rib angle θ.

Figure 4:
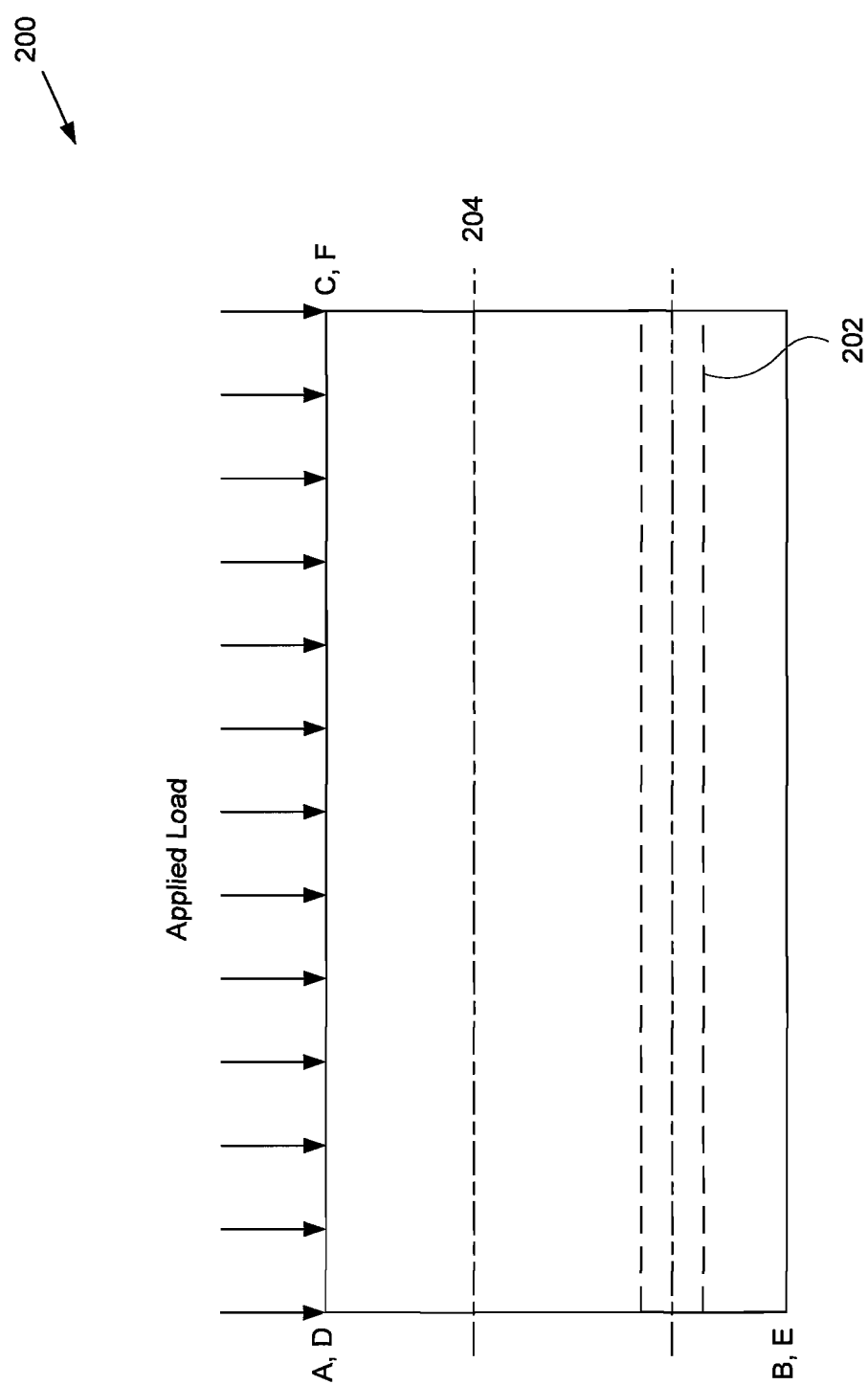
FIG. 4 is a diagram of the reference specimen reinforced concrete reference specimen in a side view loaded in a test condition, according to one example.

FIG. 4 is a diagram of the reinforced concrete reference specimen 200 in a side view loaded in a test condition, according to one example. A load may be applied to the reinforced concrete reference specimen 200 as shown. In one example the load is a distributed load. Ultrasonic measurements may be taken using the direct technique of ultrasonic measurement with the first probe 102 and the second probe 104 disposed substantially either side of the longitudinal axis of the specimen reinforcement 202, for example, with the first probe 102 disposed along a first axis parallel to line AC on the first plane ABC and the second probe 104 disposed along a second axis parallel to line DF on the second plane DEF. Ultrasonic measurements along lines substantially parallel to line AC and that do not intersect the specimen reinforcement 202 are disposed in the PC zone, and ultrasonic measurements made along axes substantially parallel to the longitudinal axis of the specimen reinforcement 202 where the specimen reinforcement 202 likely does affect the ultrasonic measurements are likely in the RC zone. Failure is defined as a case where loading results in the reinforced concrete reference specimen 200 developing cracks and unable to support additional loading.

In another example, the total load applied may be one or more point loads.

Figure 5:
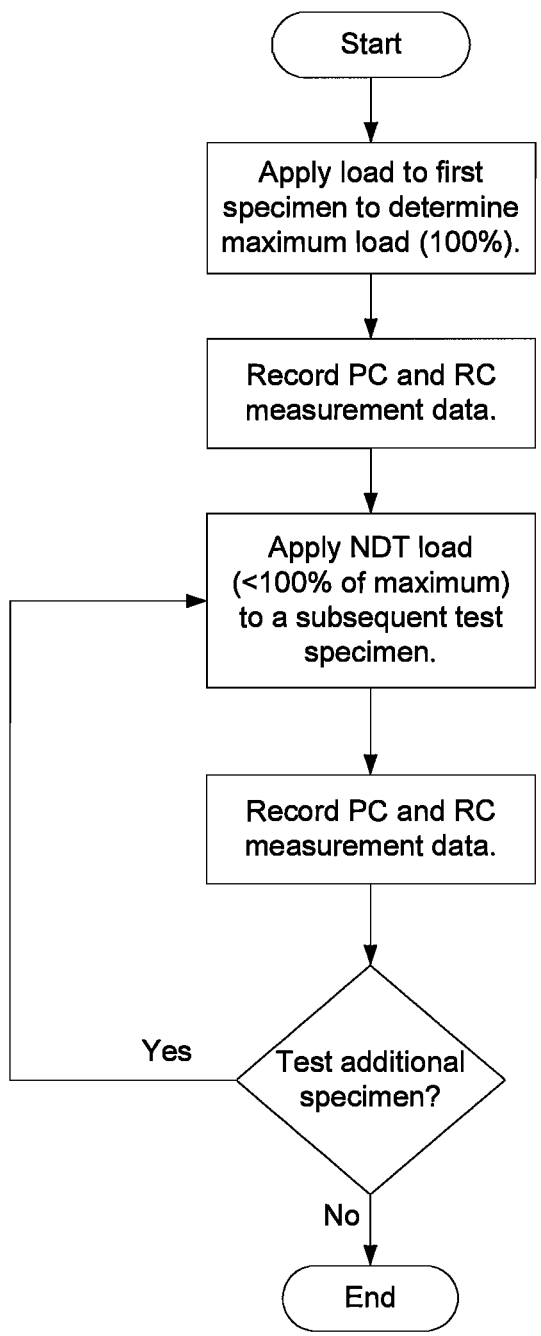
FIG. 5 is a process of obtaining test data for comparison, according to one example.

FIG. 5 is a process of obtaining test data for comparison, according to one example. Test data comprises two distinct sets of ultrasonic measurements for each specimen tested. A first set comprises ultrasonic measurements taken on the reinforced concrete reference specimen 200 along an axis substantially parallel to line AC of the reinforced concrete reference specimen 200 where the reinforced concrete reference specimen 200 contains substantially only PC and within which there is no RC. A second set comprises ultrasonic measurements taken on the reinforced concrete reference specimen 200 along the longitudinal axis of the specimen reinforcement 202 where the reinforced concrete reference specimen 200 contains RC.

In one case, each ultrasonic measurement may be taken using a direct technique of measurement of USPV signals, in which the first probe 102 is disposed on the first side of the reinforced concrete reference specimen 200 and the second probe 104 is disposed on the second side of the reinforced concrete reference specimen 200.

In another case, each ultrasonic measurement may be taken using an indirect technique of ultrasonic measurement of USPV signals, for example in which the first probe 102 and the second probe 104 are both disposed on the first side of the reinforced concrete reference specimen 200.

In another case, each ultrasonic measurement of reinforced concrete may be taken using a semi-direct technique of ultrasonic measurement of USPV signals, in which the first probe 102 is disposed on the first side of the reinforced concrete reference specimen 200 and the second probe 104 may be disposed on a perpendicular plane and in contact with an end of an axis of the specimen reinforcement 202.

A plurality of reinforced concrete reference specimens 200 are tested to obtain both PC and RC ultrasonic measurement data as described by FIG. 4. A first 200a is tested to failure to obtain an estimated maximum load, nominally assumed to be one hundred percent. Once the estimated maximum load is assumed, each test performed on each subsequent reinforced concrete reference specimen 200 is a Non-Destructive Test (NDT), where the reinforced concrete reference specimen 200 is subjected to an applied load of less than one hundred percent and not loaded to failure. For example, a second 200b is loaded to 25 percent of maximum load, and PC and RC ultrasonic measurements are recorded with the USPV test device 101. A third 200c is loaded to 50 percent of the maximum load, and PC and RC ultrasonic measurements are recorded with the USPV test device 101. A fourth 200d is loaded to 75 percent of the maximum load, and PC and RC ultrasonic measurements are recorded with the USPV test device 101. A fifth 200e is loaded to 90 percent of the maximum load, and PC and RC ultrasonic measurements are recorded with the USPV test device 101.

In an example of the above case, $P_{max}$ may be initially obtained by testing one concrete reference specimen 200 to failure before proceeding with additional specimens. A number of test concrete reference specimens may each be tested to progressively greater loads as zero load, $0.25P_{max}$, $0.5\ P_{max}$, $0.75\ P_{max}$, and $P_{max}$ with USPVT measurements at each load taken as described in FIG. 4. $P_{max}$ may be initially obtained by testing. In one experiment, five concrete reference specimens labeled as beams 1 through 5 in Table 1 were each measured at nine locations spaced apart at 55 mm intervals along a PC axis and an RC axis in an unloaded state using the USPV techniques described to obtain baseline readings (each reading stated is an average of six readings taken at the same location of each specimen) of wave velocity in each PC and RC regimes. In this case the wave velocity used was 54 kHz.

TABLE 1

UPV Readings from RC & PC Zones before the Application of Loading

| Reading | RC T (μs) | PC V (m/s) | RC T (μs) | PC V (m/s) | RC T (μs) | PC V (m/s) | RC T (μs) | PC V (m/s) |
|---|---|---|---|---|---|---|---|---|
| | BEAM-1 | | | | BEAM-2 | | | |
| 1 | 20.8 | 4807 | 19.9 | 5025 | 19.9 | 5025 | 20.1 | 4975 |
| 2 | 19.9 | 5025 | 20.3 | 4926 | 19.9 | 5025 | 19.8 | 5050 |
| 3 | 19.9 | 5025 | 20 | 5000 | 20.4 | 4901 | 19.9 | 5025 |
| 4 | 20.4 | 4901 | 20.4 | 4901 | 19.9 | 5025 | 20.4 | 4901 |
| 5 | 20.4 | 4901 | 20.4 | 4901 | 20.4 | 4901 | 20.4 | 4901 |
| 6 | 20.4 | 4901 | 20.3 | 4926 | 19.9 | 5025 | 19.8 | 5050 |
| 7 | 20.3 | 4926 | 19.4 | 5154 | 19.8 | 5050 | 19.8 | 5050 |
| 8 | 20.3 | 4926 | 20.3 | 4926 | 20.8 | 4807 | 19.9 | 5025 |
| 9 | 20.4 | 4901 | 20.4 | 4901 | 19.8 | 5050 | 20.4 | 4901 |
| | BEAM-3 | | | | BEAM-4 | | | |
| 1 | 19.9 | 5025 | 20.3 | 4926 | 20.2 | 4950 | 19.8 | 5050 |
| 2 | 20.3 | 4926 | 20.4 | 4901 | 20 | 5000 | 19.8 | 5050 |
| 3 | 19.9 | 5025 | 20.4 | 4901 | 20.3 | 4926 | 19.9 | 5025 |
| 4 | 19.8 | 5050 | 19.9 | 5025 | 20 | 5000 | 19.8 | 5050 |
| 5 | 20.3 | 4926 | 20.1 | 4975 | 20.4 | 4901 | 19.8 | 5050 |
| 6 | 19.9 | 5025 | 20.4 | 4901 | 20.3 | 4926 | 19.9 | 5025 |
| 7 | 19.8 | 5050 | 19.8 | 5050 | 20.4 | 4901 | 19.9 | 5025 |

TABLE 1-continued

UPV Readings from RC & PC Zones before the Application of Loading

| 5 | 19.8 | 5050 | 19.8 | 5050 |
| 6 | 20.4 | 4901 | 19.9 | 5025 |
| 7 | 19.9 | 5025 | 19.9 | 5025 |
| 8 | 21.7 | 4608 | 20.4 | 4901 |
| 9 | 20.4 | 4901 | 19.8 | 5050 |

Figure 6A:
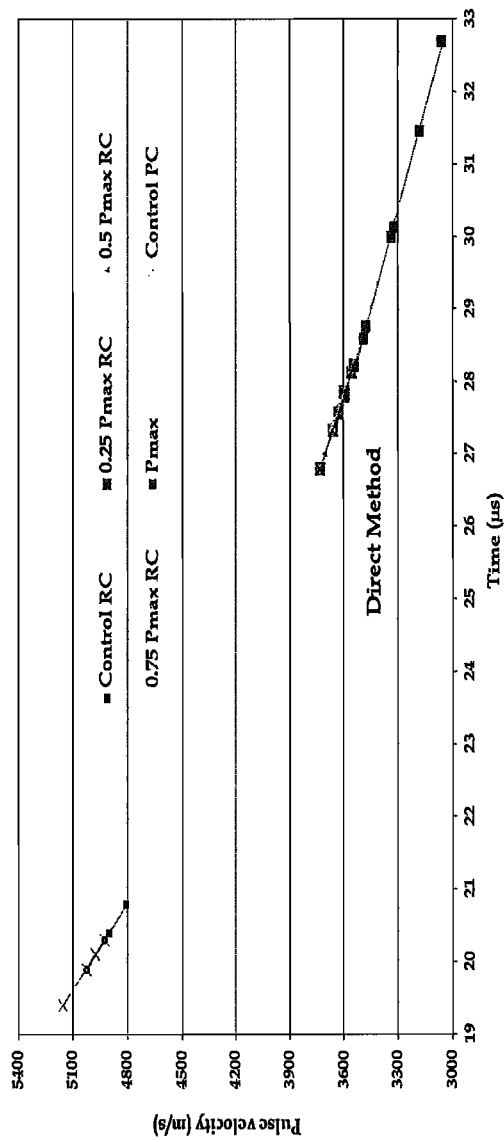
FIG. 6A is a graph of ultrasonic measurements tabulated in Table 1 and Table 2, according to one example.
Figure 6B:
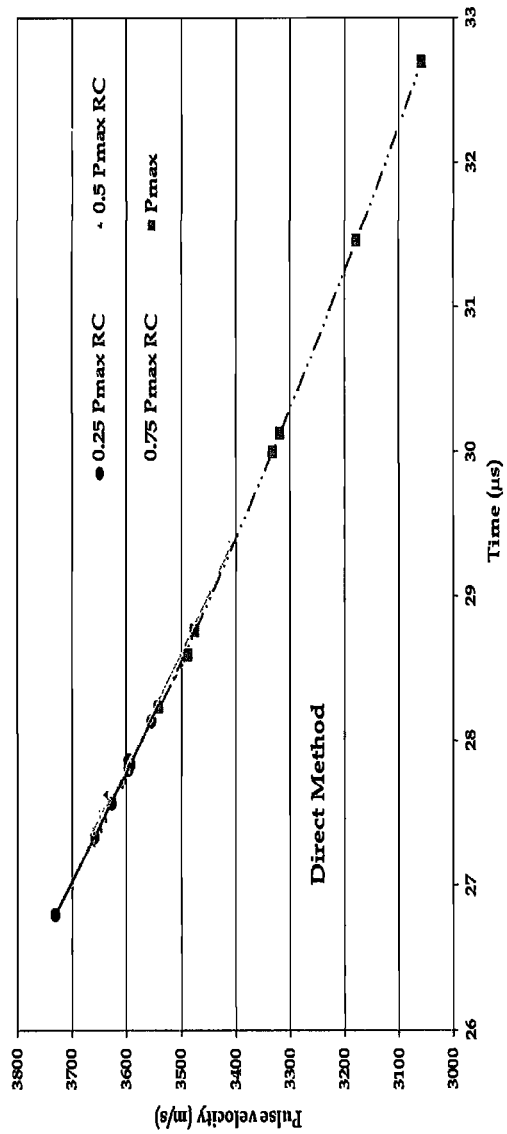
FIG. 6B is a graph of ultrasonic measurements tabulated in Table 2, according to one example.

Each concrete reference specimen was then loaded to 0.25 $P_{max}$, 0.5 $P_{max}$, and 0.75 $P_{max}$ with measurements taken at approximately the same locations on each. The results are shown in Table 2 and plotted on the graphs illustrated by FIGS. 6A and 6B, showing a strong correlation between increased loading and decreased wave velocity (and to an increase in signal transmission time). The data show there is a clear relationship between increased loading and wave velocity. This can be attributed to the development and growth of cracks and voids within each concrete reference specimen 200, particularly where concrete is bonded to a steel specimen reinforcement 202. As loading increases, cracks and voids propagate and bond quality continues to deteriorate as indicated by decreased wave velocity and increased signal transmission times.

TABLE 2

UPV Readings from RC & PC Zones after the Application of Load

Description
Reinforced Concrete Beams
Loading

| Reading Point | 0.25 $P_{max}$ | | 0.5 $P_{max}$ | | 0.75 $P_{max}$ | | $P_{max}$ | |
|---|---|---|---|---|---|---|---|---|
| | $T_{ime}$ (μs) | $V_{elocity}$ (m/s) | $T_{ime}$ (μs) | $V_{elocity}$ (m/s) | $T_{ime}$ (μs) | $V_{elocity}$ (m/s) | $T_{ime}$ (μs) | $V_{elocity}$ (m/s) |
| 1 | 26.8 | 3731 | 28.1 | 3717 | 27.4 | 3660 | 32.7 | 3058 |
| 2 | 27.9 | 3589 | 27.6 | 3619 | 29.0 | 3444 | 31.5 | 3178 |
| 3 | 27.3 | 3659 | 27.9 | 3506 | 28.2 | 3542 | 28.6 | 3497 |
| 4 | 28.1 | 3555 | 27.7 | 3520 | 29.4 | 3405 | 27.4 | 3654 |
| 5 | 29.4 | 3398 | 27.5 | 3641 | 27.7 | 3606 | 30.1 | 3319 |
| 6 | 28.2 | 3542 | 29.9 | 3320 | 27.5 | 3636 | 30.0 | 3333 |
| 7 | 27.6 | 3628 | 27.8 | 3597 | 28.8 | 3472 | 30.0 | 3333 |
| 8 | 27.8 | 3593 | 27.8 | 3563 | 28.2 | 3550 | 28.8 | 3476 |
| 9 | 27.8 | 3597 | 27.4 | 3650 | 27.4 | 3654 | 28.2 | 3542 |
| $T_{min}$ & $V_{min}$ | 26.8 | 3398 | 27.4 | 3320 | 27.4 | 3405 | 27.4 | 3058 |
| $T_{max}$ & $V_{max}$ | 29.4 | 3731 | 29.9 | 3717 | 29.4 | 3654 | 32.7 | 3654 |
| Standard Deviation(SD) | 0.7 | 91 | 0.7 | 91 | 0.7 | 93 | 1.7 | 186 |

TABLE 1-continued

UPV Readings from RC & PC Zones before the Application of Loading

| 8 | 19.9 | 5025 | 19.8 | 5050 | 19.8 | 5050 | 19.3 | 5181 |
| 9 | 19.9 | 5025 | 20.3 | 4926 | 20.3 | 4926 | 19.9 | 5025 |

BEAM-5

| Reading | RC T (μs) | RC V (m/s) | PC T (μs) | PC V (m/s) |
|---|---|---|---|---|
| 1 | 20.3 | 4926 | 19.8 | 5050 |
| 2 | 19.9 | 5025 | 20.4 | 4901 |
| 3 | 19.8 | 5050 | 20.2 | 4950 |
| 4 | 19.9 | 5025 | 19.9 | 5025 |

FIG. 6A is a graph of ultrasonic measurements tabulated in Table 1 and Table 2, according to one example. FIG. 6A shows the unloaded control state of concrete reference specimens 200 possesses a higher wave velocity than that of any loaded state.

FIG. 6B is a graph of ultrasonic measurements tabulated in Table 2, according to one example. The graph of FIG. 6B illustrates the portion of the graph of FIG. 6A that shows pulse velocities from loaded states of the concrete reference specimens 200.

Figure 6C:
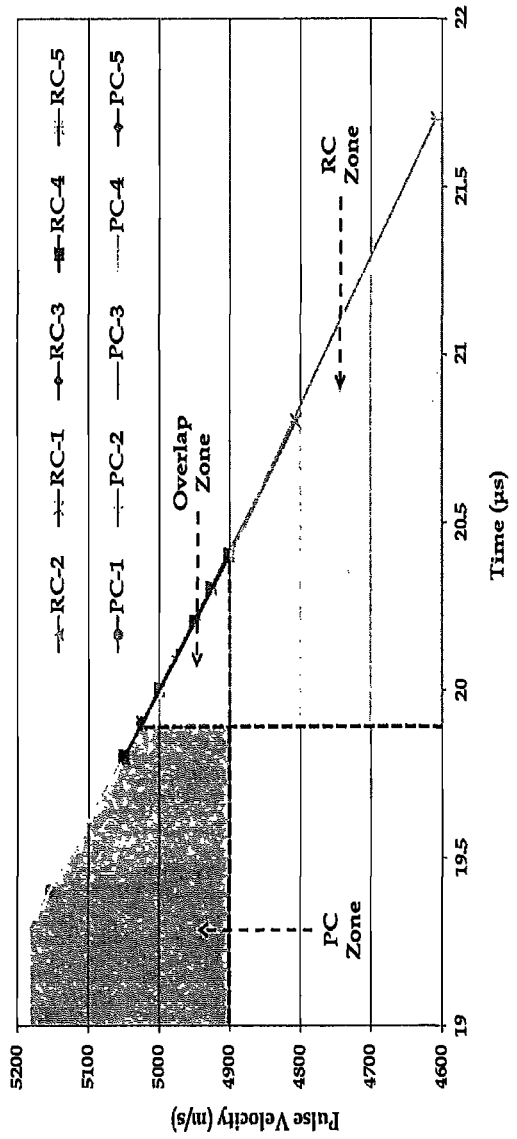
FIG. 6C is a graphical representation of ultrasonic measurements obtained experimentally through a USPV test process, according to one example.

FIG. 6C is a graphical representation of ultrasonic measurements obtained experimentally through a USPV test process, according to one example. A triangular area is bounded by a vertical line intersecting a point on an extrapolated wave velocity line in a region where wave velocity readings from both RC and PC ultrasonic measurements are located, and by a horizontal line along the wave velocity (Y-axis) that intersects a point at another end of the spectrum on the extrapolated line in the region where wave velocity readings from both RC and PC ultrasonic measurements are also located.

Ultrasonic measurement data sets plotted on the graph represent RC and PC zone measurements for five specimens in an unloaded state, denoted as RC-1 through RC-5 and PC-1 through PC-5. Measurements of time to detect transmitted ultrasonic signals were obtained from testing a plurality of reinforced concrete reference specimen 200, with each reinforced concrete reference specimen 200 loaded at various levels ranging from 25% to 90% of maximum load, as described by FIG. 5. The results were plotted to determine the range for PC and RC ultrasonic measurements. A range where PC ultrasonic measurements and RC ultrasonic measurements overlap on the graph provide an indication of bond quality between an anchor bolt 130 and concrete. Air pockets and porosity within the reinforced concrete reference specimen 200, as well as the presence of other materials or impurities, may slow ultrasonic transmission of ultrasonic signals and increase time for the USPV test device 101 to detect rebounding ultrasonic signals. The increased time delay can indicate the presence of internal imperfections within some areas of the reinforced concrete reference specimen 200.

Experiment has shown the amount of overlap between ultrasonic measurement data sets of the PC and the RC zones increases with increased load on the reinforced concrete reference specimen 200, indicating that the larger the overlap area for an unstressed reinforced concrete reference specimen 200, the less the compressive strength, and therefore the lower the quality of the bond, and the higher the likelihood that voids and cracks are present within the reinforced concrete reference specimen 200. Conversely, the smaller an overlapping area, the higher the compressive strength of the reinforced concrete reference specimen 200.

Figure 7:
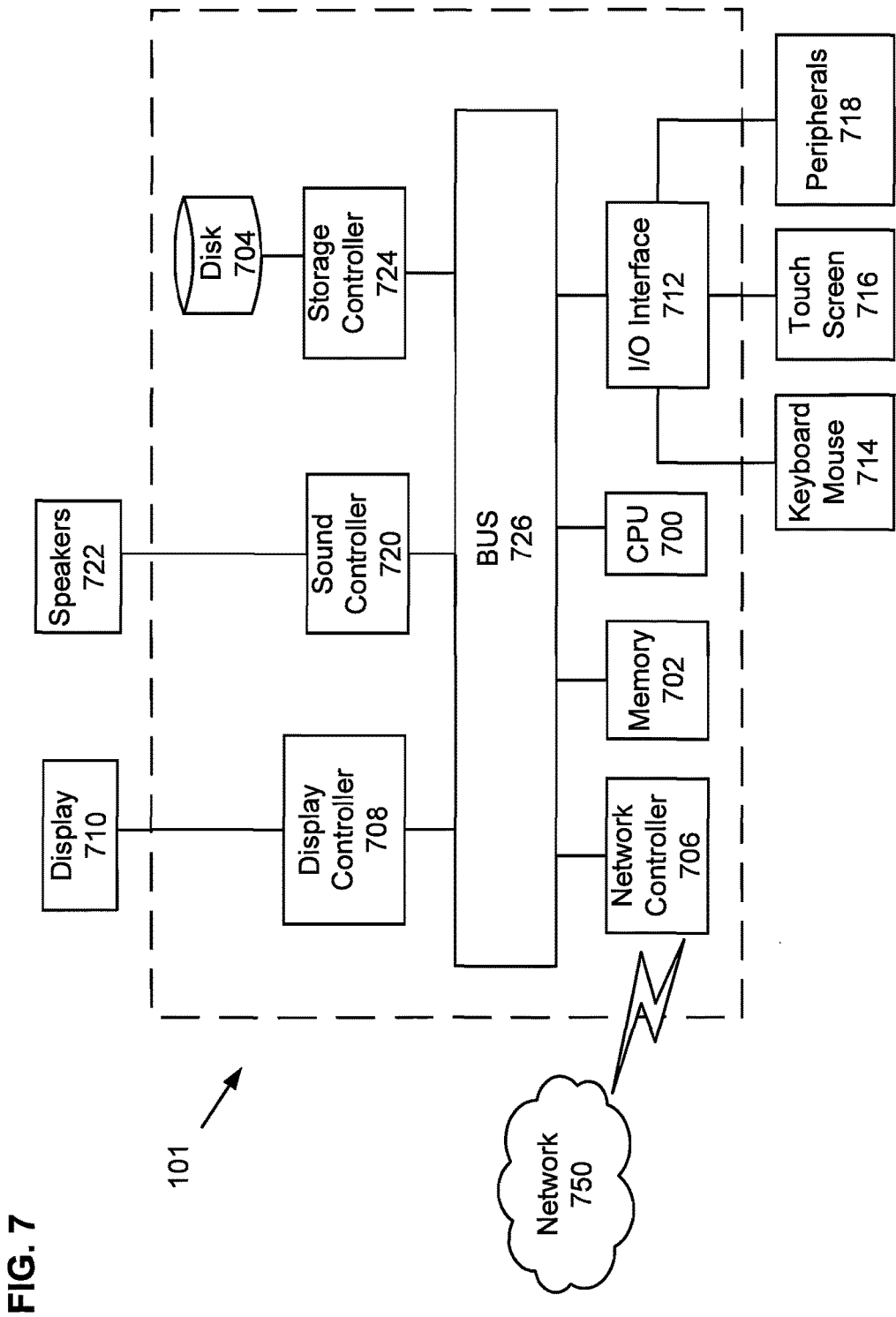
FIG. 7 provides a hardware description of the USPV test device 101 according to exemplary embodiments.

FIG. 7 provides a hardware description of the USPV test device 101 according to exemplary embodiments. The USPV test device 101 includes a CPU 700 which performs the processes described above/below. The process data and instructions may be stored in memory 702. These processes and instructions may also be stored on a storage medium disk 704 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the USPV test device 101 communicates, such as a server or computer.

Further, the claimed advancements may be provided as a utility application, background daemon, or component of an operating system, or combination thereof, executing in conjunction with CPU 700 and an operating system such as Microsoft Windows 7, UNIX, Solaris, LINUX, Apple MAC-OS and other systems known to those skilled in the art.

The hardware elements in order to achieve the USPV test device 101 may be realized by various circuitry elements, known to those skilled in the art. For example, CPU 700 may be a Xenon or Core processor from Intel of America or an Opteron processor from AMD of America, or may be other processor types that would be recognized by one of ordinary skill in the art. Alternatively, the CPU 700 may be implemented on an FPGA, ASIC, PLD or using discrete logic circuits, as one of ordinary skill in the art would recognize. Further, CPU 700 may be implemented as multiple processors cooperatively working in parallel to perform the instructions of the inventive processes described above.

The USPV test device 101 in FIG. 7 also includes a network controller 706, such as an Intel Ethernet PRO network interface card from Intel Corporation of America, for interfacing with network 750. As can be appreciated, the network 750 can be a public network, such as the Internet, or a private network such as an LAN or WAN network, or any combination thereof and can also include PSTN or ISDN sub-networks. The network 750 can also be wired, such as an Ethernet network, or can be wireless such as a cellular network including EDGE, 3G and 4G wireless cellular systems. The wireless network can also be WiFi, Bluetooth, or any other wireless form of communication that is known.

The USPV test device 101 further includes a display controller 708, such as a NVIDIA GeForce GTX or Quadro graphics adaptor from NVIDIA Corporation of America for interfacing with display 710, such as a Hewlett Packard HPL2445w LCD monitor. A general purpose I/O interface 712 interfaces with a keyboard and/or mouse 714 as well as a touch screen panel 716 on or separate from display 710. General purpose I/O interface also connects to a variety of peripherals 718 including printers and scanners, such as an OfficeJet or DeskJet from Hewlett Packard.

A sound controller 720 is also provided in the USPV test device 101, such as Sound Blaster X-Fi Titanium from Creative, to interface with speakers/microphone 722 thereby providing sounds and/or music.

The general purpose storage controller 724 connects the storage medium disk 704 with communication bus 726, which may be an ISA, EISA, VESA, PCI, or similar, for interconnecting all of the components of the USPV test device 101. A description of the general features and functionality of the display 710, keyboard and/or mouse 714, as well as the display controller 708, storage controller 724, network controller 706, sound controller 720, and general purpose I/O interface 712 is omitted herein for brevity as these features are known.

The exemplary circuit elements described in the context of the present disclosure may be replaced with other elements and structured differently than the examples provided herein. Moreover, circuitry configured to perform features described herein may be implemented in multiple circuit units (e.g., chips), or the features may be combined in circuitry on a single chipset, as shown on FIG. 8.

Figure 8:
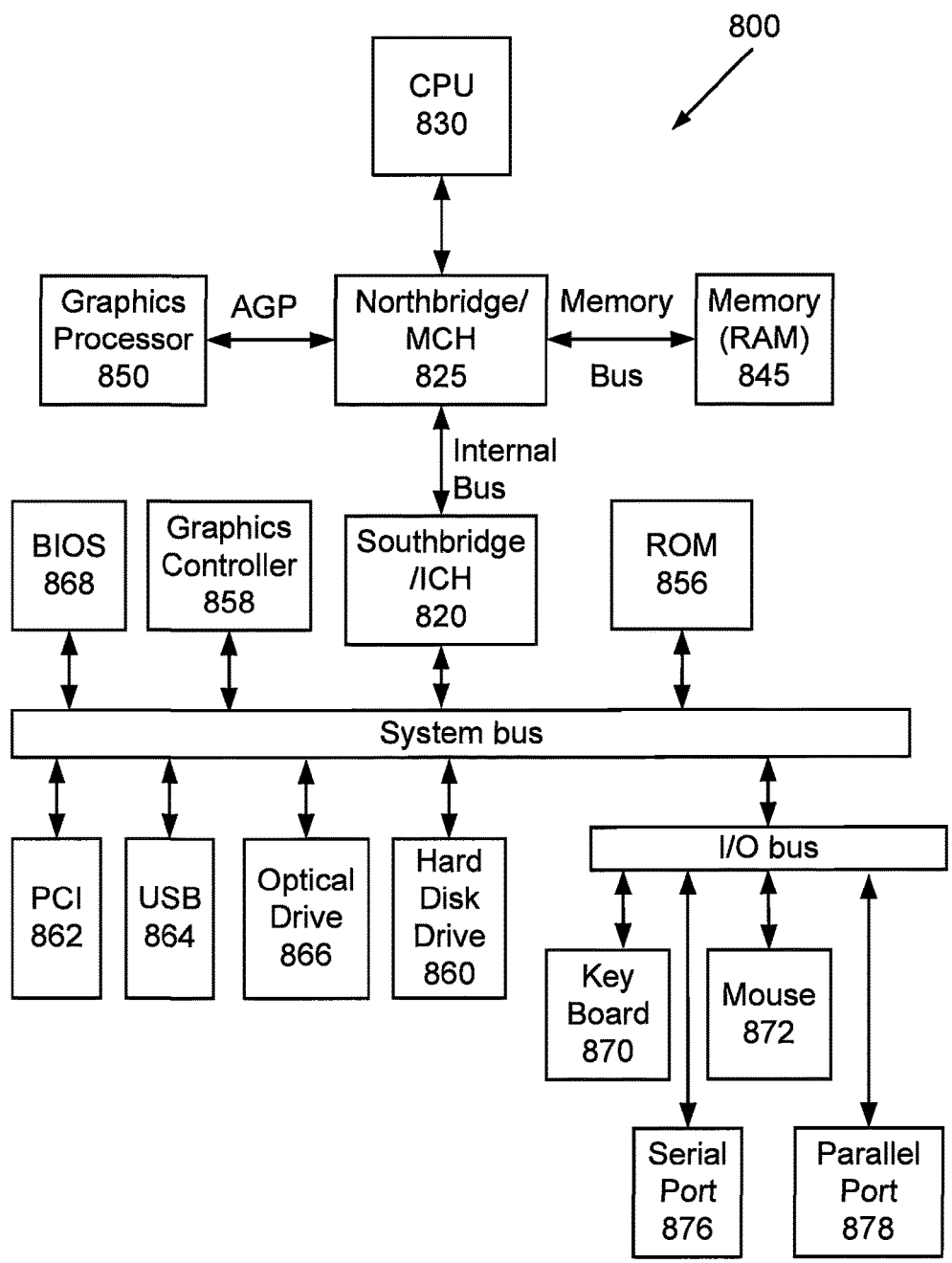
FIG. 8 shows a schematic diagram of a data processing system, according to certain embodiments, for performing USPV tests.

FIG. 8 shows a schematic diagram of a data processing system, according to certain embodiments, for performing USPV tests. The data processing system is an example of a computer in which code or instructions implementing the processes of the illustrative embodiments may be located.

The data processing system 800 employs a hub architecture including a north bridge and memory controller hub (NB/MCH) 825 and a south bridge and input/output (I/O) controller hub (SB/ICH) 820. The central processing unit (CPU) 830 is connected to NB/MCH 825. The NB/MCH 825 also connects to the memory 845 via a memory bus, and connects to the graphics processor 850 via an accelerated graphics port (AGP). The NB/MCH 825 also connects to the SB/ICH 820 via an internal bus (e.g., a unified media interface or a direct media interface). The CPU Processing unit 830 may contain one or more processors and even may be implemented using one or more heterogeneous processor systems.

According to certain implementations, the instruction set architecture of the CPU 830 can use a reduced instruction set architecture, a complex instruction set architecture, a vector processor architecture, a very large instruction word architecture. Furthermore, the CPU 830 can be based on the Von Neuman model or the Harvard model. The CPU 830 can be a digital signal processor, an FPGA, an ASIC, a PLA, a PLD, or a CPLD. Further, the CPU 830 can be an x86 processor by Intel or by AMD; an ARM processor, a Power architecture processor by, e.g., IBM; a SPARC architecture processor by Sun Microsystems or by Oracle; or other known CPU architecture.

Referring again to FIG. 8, the data processing system 800 can include that the SB/ICH 820 is coupled through a system bus to an I/O Bus, a read only memory (ROM) 856, universal serial bus (USB) port 864, a flash binary input/output system (BIOS) 868, and a graphics controller 858. PCI/PCIe devices can also be coupled to SB/ICH 820 through a PCI bus 862.

The PCI devices may include, for example, Ethernet adapters, add-in cards, and PC cards for notebook computers. The Hard disk drive 860 and CD-ROM 866 can use, for example, an integrated drive electronics (IDE) or serial advanced technology attachment (SATA) interface. In one implementation the I/O bus can include a super I/O (SIO) device.

Further, the hard disk drive (HDD) 860 and optical drive 866 can also be coupled to the SB/ICH 820 through a system bus. In one implementation, a keyboard 870, a mouse 872, a parallel port 878, and a serial port 876 can be connected to the system bust through the I/O bus. Other peripherals and devices that can be connected to the SB/ICH 820 using a mass storage controller such as SATA or PATA, an Ethernet port, an ISA bus, a LPC bridge, SMBus, a DMA controller, and an Audio Codec.

Moreover, the present disclosure is not limited to the specific circuit elements described herein, nor is the present disclosure limited to the specific sizing and classification of these elements. For example, the skilled artisan will appreciate that the circuitry described herein may be adapted based on changes on battery sizing and chemistry, or based on the requirements of the intended back-up load to be powered.

The functions and features described herein may also be executed by various distributed components of a system. For example, one or more processors may execute these system functions, wherein the processors are distributed across multiple components communicating in a network. The distributed components may include one or more client and server machines, which may share processing, as shown on FIG. 9, in addition to various human interface and communication devices (e.g., display monitors, smart phones, tablets, personal digital assistants (PDAs)). The network may be a private network, such as a LAN or WAN, or may be a public network, such as the Internet. Input to the system may be received via direct user input and received remotely either in real-time or as a batch process. Additionally, some implementations may be performed on modules or hardware not identical to those described. Accordingly, other implementations are within the scope that may be claimed.

Figure 9:
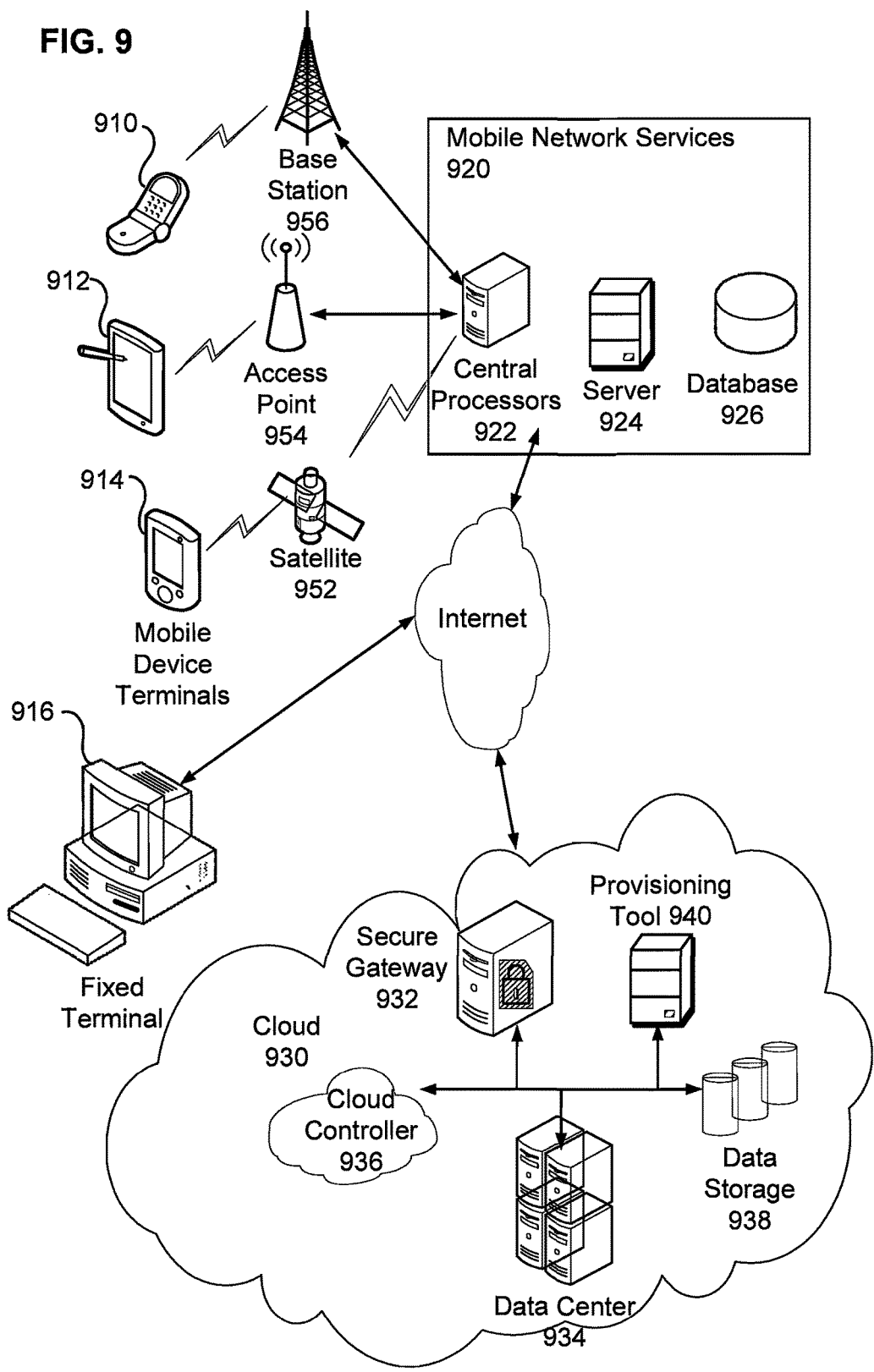
FIG. 9 shows an example of cloud computing, wherein users access the cloud through mobile device terminals or fixed terminals that are connected to the internet.

FIG. 9 shows an example of cloud computing, wherein users access the cloud through mobile device terminals or fixed terminals that are connected to the internet. The mobile device terminals can include a cell phone 910, and tablet computer 912, and a smartphone 914, for example. The mobile device terminals can connect to a mobile network service 920 through a wireless channel such as a base station 956 (e.g., an Edge, 3G, 4G, or LTE Network), an access point 954 (e.g., a femto cell or WiFi network), or a satellite connection 952. In one implementation, signals from the wireless interface to the mobile device terminals (e.g., the base station 956, the access point 954, and the satellite connection 952) are transmitted to a mobile network service 920, such as an EnodeB and radio network controller, UMTS, or HSDPA/HSUPA. Mobile users' requests and information are transmitted to central processors 922 that are connected to servers 924 providing mobile network services, for example. Further, mobile network operators can provide service to mobile uses as authentication, authorization, and accounting based on home agent and subscribers' data stored in databases 926, for example. After that, the subscribers' requests are delivered to a cloud 930 through the internet.

A user can also access the cloud through a fixed terminal 916, such as a desktop or laptop computer or workstation that is connected to the internet via a wired network connection or a wireless network connection. The network can be a public or a private network such as an LAN or WAN network. The network can be wireless such as a cellular network including EDGE, 3G and 4G wireless cellular systems. The wireless network 930 can also be Wi-Fi, Bluetooth, or any other wireless form of communication that is known.

The user's terminal, such as mobile user terminals and fixed user terminals, provides to the user a mechanism to connect via the internet to the cloud 930 and to receive output from the cloud 930, which is communicated and displayed at the user's terminal. In the cloud 930, a cloud controller 936 processes the request to provide users with the corresponding cloud services. These services are provided using the concepts of utility computing, virtualization, and service-oriented architecture.

In one implementation, the cloud 930 is accessed via a user interface such as a secure gateway 932. The secure gateway 932 can, for example, provide security policy enforcement points placed between cloud service consumers and cloud service providers to interject enterprise security policies as the cloud-based resources are accessed. Further, the secure gateway 932 can consolidate multiple types of security policy enforcement, including, for example, authentication, single sign-on, authorization, security token mapping, encryption, tokenization, logging, alerting, and API control. The could 930 can provide, to users, computational resources using a system of virtualization, wherein processing and memory requirements can be dynamically allocated and dispersed among a combination of processors and memories to create a virtual machine that is more efficient at utilizing available resources. Virtualization creates an appearance of using a single seamless computer even though multiple computational resources and memories can be utilized according increases or decreases in demand. In one implementation, virtualization is achieved using a provisioning tool 940 that prepares and equips the cloud resources such as the processing center 934 and data storage 938 to provide services to the users of the cloud 930. The processing center 934 can be a computer cluster, a data center, a main frame computer, or a server farm. In one implementation, the processing center 934 and data storage 938 are collocated.

The above-described hardware description is a non-limiting example of corresponding structure for performing the functionality described herein.

Thus, the foregoing discussion discloses and describes merely exemplary embodiments of the present application. As will be understood by those skilled in the art, the present disclosure may be embodied in other specific forms without departing from the spirit or essential characteristics thereof. Accordingly, the disclosure of the present application is intended to be illustrative, but not limiting on scope, including a scope of the claims. The disclosure, including any readily discernable variants of the teachings herein, define, in part, the scope of the foregoing claim terminology such that no inventive subject matter is dedicated to the public.

What is claimed is:

1. An apparatus for detecting anchor bolt pullout strength, the apparatus comprising:
   circuitry configured to process ultrasonic measurement signals in at least one of a direct, an indirect, and a semi-direct measurement technique;
   a first probe connected to the circuitry;
   a second probe connected to the circuitry;
   a memory for storing data detected by the first and the second probe, the memory connected to the circuitry;
   a data connection connected to the circuitry and configured to be in communication with an external network; and
   a Schmidt Hammer configured to measure a compressive strength of concrete, the circuitry configured to detect measurements made by the Schmidt Hammer including a mean of rebound number readings,
   wherein, if the circuitry determines that the mean of rebound number readings is less than a value or within a range of values, an ultrasonic signal is transmitted by the circuitry through the first probe and rebounded by the second probe when the first and second probes are positioned on the concrete, the circuitry detecting a time duration to receive the rebounded signal at the second probe, storing the time duration to the memory, and comparing the time duration to reference measurement data to indicate an overlap between measurement data corresponding to respective pure concrete and reinforced concrete zones of the concrete, the reference measurement data stored in at least one of the memory and the external network.

2. The apparatus according to claim 1, wherein:
the circuitry is configured to include maximum likelihood detection to further analyze ultrasonic measurement results.

3. The apparatus according to claim 1, further comprising:
a memory, the memory including stored reference measurement data for a plurality of reinforced concrete specimens.

4. The apparatus according to claim 1, further comprising:
at least one of a haptic, an audio, and a visual indicator, wherein
the circuitry is configured to activate at least one of the haptic, the audio, and the visual indicator to indicate at least one of a status of the apparatus and a recommended action as a result of measurement results detected.

5. The apparatus according to claim 1, further comprising:
at least one indicator light, wherein
the circuitry is configured to illuminate at least one indicator light to indicate at least one of a status of the apparatus and a recommended action as a result of measurement results detected.

6. The apparatus according to claim 1, wherein:
the data connection is a physical connection.

7. The apparatus according to claim 1, wherein:
the data connection is a wireless connection.

* * * * *